(12) United States Patent
Roe et al.

(10) Patent No.: US 6,780,197 B2
(45) Date of Patent: Aug. 24, 2004

(54) APPARATUS AND METHODS FOR DELIVERING A VASCULAR CLOSURE DEVICE TO A BODY LUMEN

(75) Inventors: Steven N. Roe, San Mateo, CA (US); Richard S. Ginn, San Jose, CA (US); W. Martin Belef, San Jose, CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 570 days.

(21) Appl. No.: 09/732,835

(22) Filed: Dec. 7, 2000

(65) Prior Publication Data

US 2002/0026208 A1 Feb. 28, 2002

Related U.S. Application Data

(63) Continuation-in-part of application No. 09/610,238, filed on Jul. 5, 2000, which is a continuation-in-part of application No. 09/478,179, filed on Jan. 5, 2000, now Pat. No. 6,197,042.

(51) Int. Cl.$^7$ .............................................. A61B 17/04
(52) U.S. Cl. ....................... 606/213; 606/139; 606/142; 606/219
(58) Field of Search ................................ 606/213, 139, 606/142, 144, 148, 214, 219; 227/175.1, 179.1

(56) References Cited

U.S. PATENT DOCUMENTS

| | | |
|---|---|---|
| 3,586,002 A | 6/1971 | Wood |
| 3,604,425 A | 9/1971 | LeRoy |
| 3,757,629 A | 9/1973 | Schneider |
| 3,805,337 A | 4/1974 | Branstetter |
| 4,192,315 A | 3/1980 | Hilzinger et al. |
| 4,217,902 A | 8/1980 | March |
| 4,396,139 A | 8/1983 | Hall et al. |
| 4,485,816 A | 12/1984 | Krumme |
| 4,505,274 A | 3/1985 | Speelman |
| 4,586,503 A | 5/1986 | Kirsch et al. |
| 4,777,950 A | 10/1988 | Kees, Jr. |

(List continued on next page.)

FOREIGN PATENT DOCUMENTS

EP 0 774 237 A2 5/1997

OTHER PUBLICATIONS

PCT Publication No. WO 99/62408 entitled, "Vascular Port device", Dec. 9, 1999.
PCT Publication No. WO 00/060029 entitled, "Expansile Device for Use in Blood Vessels and Tracts in the Body and Method", Feb. 10, 2000.

(List continued on next page.)

Primary Examiner—Kathryn Odland
(74) Attorney, Agent, or Firm—Orrick, Herrington & Sutcliffe LLP; James W. Geriak

(57) ABSTRACT

An apparatus for delivering a closure element into a puncture communicating with a blood vessel includes an introducer sheath, and a locator member disposed within the sheath, the locator member having a distal portion extending distally beyond the distal end of the sheath. A plurality of splines are provided on the distal portion of the locator member, the splines being selectively expandable between an axial collapsed configuration and a transverse expanded configuration. An actuator is coupled to the locator member for controllably expanding the splines. A housing is slidably disposed on the sheath for deploying a closure element, such as a vascular clip. The locator actuator may automatically collapse the splines upon advancement of the housing.

41 Claims, 6 Drawing Sheets

U.S. PATENT DOCUMENTS

| | | |
|---|---|---|
| 4,860,746 A | 8/1989 | Yoon |
| 4,865,026 A | 9/1989 | Barrett |
| 4,917,087 A | 4/1990 | Walsh et al. |
| 4,950,258 A | 8/1990 | Kawai et al. |
| 5,007,921 A | 4/1991 | Brown |
| 5,026,390 A | 6/1991 | Brown |
| 5,053,008 A | 10/1991 | Bajaj |
| 5,108,420 A | 4/1992 | Marks |
| 5,156,609 A | 10/1992 | Nakao et al. |
| 5,176,648 A | 1/1993 | Holmes et al. |
| 5,192,302 A | 3/1993 | Kensey et al. |
| 5,222,974 A | 6/1993 | Kensey et al. |
| 5,275,616 A | 1/1994 | Fowler |
| 5,304,184 A | 4/1994 | Hathaway et al. |
| 5,334,217 A | 8/1994 | Das |
| 5,366,458 A | 11/1994 | Korthoff et al. |
| 5,478,354 A | 12/1995 | Tovey et al. |
| 5,507,755 A | 4/1996 | Gresl et al. |
| 5,527,322 A | 6/1996 | Klein et al. |
| 5,674,231 A | 10/1997 | Green et al. |
| 5,683,405 A | 11/1997 | Yacoubian et al. |
| 5,695,505 A | 12/1997 | Yoon |
| 5,782,844 A | 7/1998 | Yoon et al. |
| 5,782,860 A | 7/1998 | Epstein et al. |
| 5,782,861 A | 7/1998 | Cragg et al. |
| 5,810,846 A | 9/1998 | Virnich et al. |
| 5,810,851 A | 9/1998 | Yoon |
| 5,817,113 A | 10/1998 | Gifford |
| 5,820,631 A | 10/1998 | Nobles |
| 5,830,125 A | 11/1998 | Scribner et al. |
| 5,879,366 A | 3/1999 | Shaw et al. |
| 5,910,155 A | 6/1999 | Ratcliff et al. |
| 5,922,009 A | 7/1999 | Epstein et al. |
| 5,951,589 A | 9/1999 | Epstein et al. |
| 5,964,782 A | 10/1999 | LaFontaine et al. |
| 5,984,934 A | 11/1999 | Ashby et al. |
| 6,007,563 A | 12/1999 | Nash et al. |
| 6,036,720 A | 3/2000 | Abrams et al. |
| 6,045,570 A | 4/2000 | Epstein et al. |
| 6,056,769 A | 5/2000 | Epstein et al. |
| 6,056,770 A | 5/2000 | Epstein et al. |
| 6,063,085 A | 5/2000 | Tay et al. |
| 6,077,281 A | 6/2000 | Das |
| 6,077,291 A | 6/2000 | Das |
| 6,080,182 A | 6/2000 | Shaw |
| 6,080,183 A | 6/2000 | Tsugita et al. |
| 6,120,524 A | 9/2000 | Taheri |
| 6,277,140 B2 * | 8/2001 | Ginn et al. .................. 606/213 |
| 6,334,865 B1 * | 1/2002 | Redmond et al. ........... 606/213 |
| 6,409,739 B1 * | 6/2002 | Nobles et al. ............... 606/148 |
| 6,547,806 B1 * | 4/2003 | Ding ........................... 606/213 |
| 2002/0026215 A1 * | 2/2002 | Redmond et al. ........... 606/213 |
| 2002/0072768 A1 * | 6/2002 | Ginn ........................... 606/213 |
| 2002/0077657 A1 * | 6/2002 | Ginn et al. .................. 606/213 |
| 2002/0188318 A1 * | 12/2002 | Carley et al. ................ 606/213 |
| 2002/0193808 A1 * | 12/2002 | Belef et al. .................. 606/139 |
| 2003/0078598 A1 * | 4/2003 | Ginn et al. .................. 606/142 |
| 2003/0125766 A1 * | 7/2003 | Ding ........................... 606/213 |
| 2003/0158577 A1 * | 8/2003 | Ginn et al. .................. 606/213 |
| 2003/0158578 A1 * | 8/2003 | Pantages et al. ............ 606/213 |

OTHER PUBLICATIONS

PCT Publication No. WO 00/07640 entitled, "Vascular Suction Cannula, Dilator and Surgical Stapler", Feb. 17, 2000.
PCT Publication No. WO 00/07640, "Vascular Suction Cannula, Dialator and Surgical Stapler", Feb. 17, 2000.
PCT Publication No. WO 00/56227, entitled "Advanced Closure Device", Sep. 28, 2000.
PCT Publication No. WO 00/56223 entitled "Vascular Closure Device", Sep. 28, 2000.
PCT Publication No. WO 99/62408 entitled "Vascular Port Device", Dec. 9, 1999.
PCT Publication No. WO 98/24374, "Vascular Wound Closure System", Yong Zhu, et al., Jun. 11, 1998.
PCT Publication No. WO 97/20505, "Vascular Wound Closure Device", Yong Zhu, et al., Jun. 12, 1997.

* cited by examiner

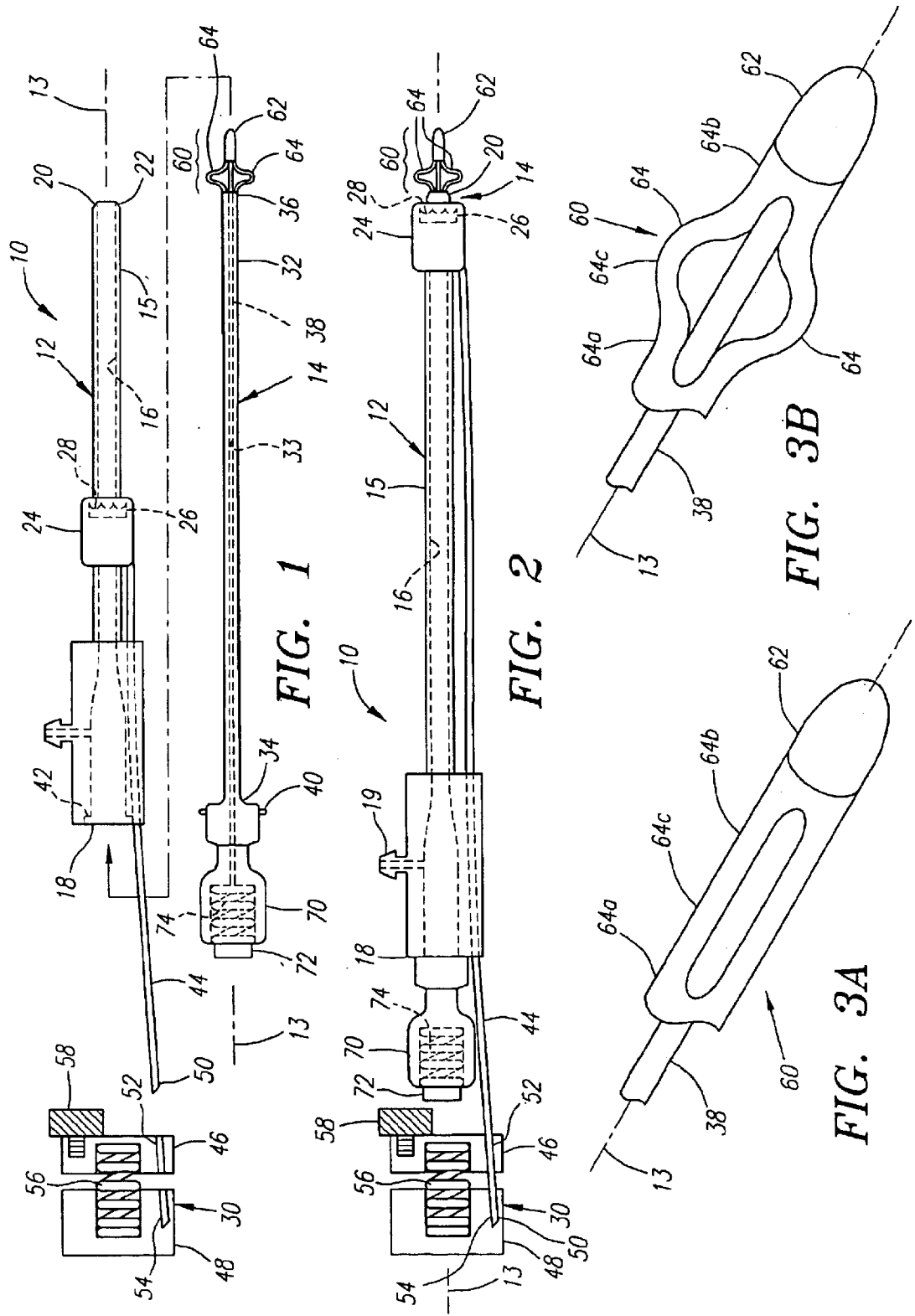

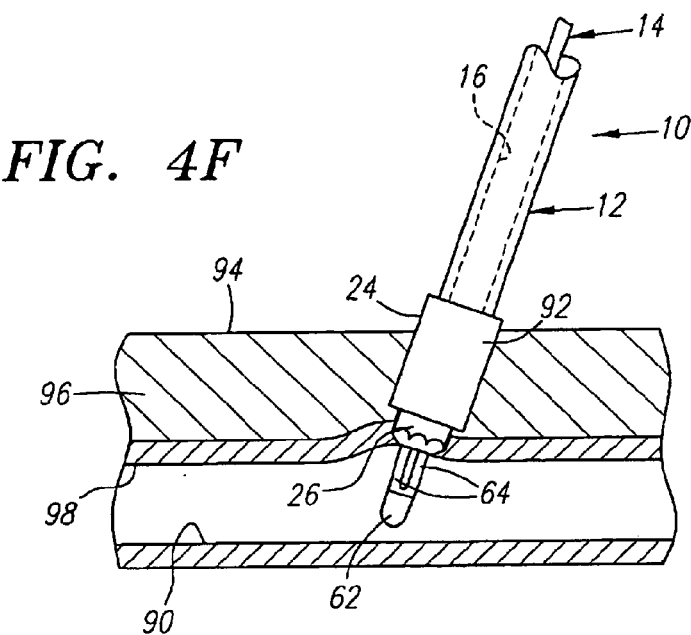
FIG. 4F
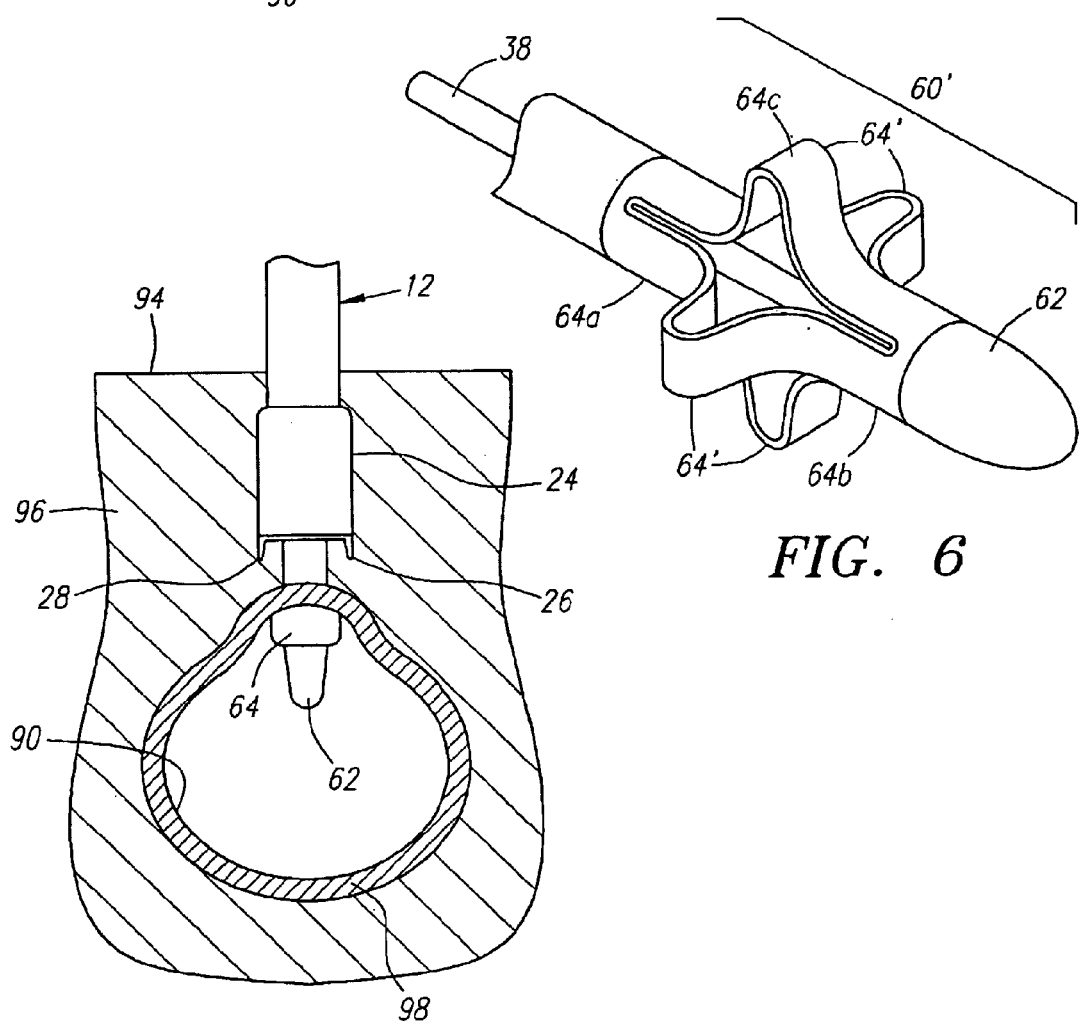
FIG. 6
FIG. 5

APPARATUS AND METHODS FOR DELIVERING A VASCULAR CLOSURE DEVICE TO A BODY LUMEN

This application is a continuation-in-part of co-pending application Ser. No. 09/610,238, filed Jul. 5, 2000, which is a continuation-in-part of application Ser. No. 09/478,179, filed Jan. 5, 2000 now U.S. Pat. No. 6,197,042, the disclosures of which are expressly incorporated herein by reference.

FIELD OF THE INVENTION

The present invention relates generally to apparatus and methods for closing and/or sealing openings into body lumens, and more particularly to apparatus and methods for delivering a vascular closure element for closing a puncture in a blood vessel formed during a diagnostic or therapeutic procedure.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

To facilitate positioning devices that are percutaneously inserted into a blood vessel, "bleed back" indicators have been suggested. For example, U.S. Pat. No. 4,317,445, issued to Robinson, discloses a flashback chamber on a first end of a cannula that communicates with a port on a second end. The second end is percutaneously introduced into a patient until the port enters the vessel, whereupon blood, under normal blood pressure, may advance along the cannula and enter the flashback chamber, thereby providing a visual indication that the vessel has been entered. This reference, however, does not discuss vascular wound closure, but is merely directed to an introducer device. In contrast, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating the deployment and deflection of a surgical clip against the vessel wall. Such a device, however, may risk engagement between the loop and the surgical clip, thereby preventing the loop from being withdrawn from the vessel.

Accordingly, apparatus and methods for delivering a device for closing a vascular puncture site would be considered useful.

SUMMARY OF THE INVENTION

The present invention is directed to apparatus and methods for closing and/or sealing openings into body lumens, and more particularly to apparatus and methods for delivering a vascular closure element for closing a puncture in a blood vessel formed during a diagnostic or therapeutic procedure.

In accordance with one aspect of the present invention, an apparatus is provided for delivering a closure element into engagement with tissue adjacent an opening into a body lumen. The apparatus includes a sheath including a lumen extending between its proximal and distal ends, and a locator member disposed within the sheath, the locator member having a distal portion extending distally beyond the distal end of the sheath. One or more positioning elements are provided on the distal portion of the locator member, the positioning elements being selectively expandable between a substantially axial collapsed configuration and a substantially transverse expanded configuration. Preferably, the positioning elements are a plurality, e.g. two or more, equally spaced, substantially flexible splines or wings configured for expanding substantially transversely to a longitudinal axis of the sheath. Each spline may have a first fixed end and a second movable end, the second end being axially movable towards the first end to cause an intermediate region of the spline to expand radially outward, thereby defining the radially expanded configuration. Alternatively, the splines may include a plurality of substantially rigid or semi-rigid elements that are hinged such that the splines may be expanded to the expanded configuration.

An actuator may be coupled to the locator member, the actuator configured for controllably expanding the positioning elements from the collapsed configuration to the expanded configuration. The actuator may include a control such that the positioning elements may be selectively expanded to one of a plurality of expanded sizes, e.g., to accommodate insertion into vessels of various sizes.

A housing may be axially slidably disposed on an exterior of the sheath, the housing configured for releasably holding a closure element, the housing being actuable for advancing the closure element distally to deploy the closure element. In a preferred embodiment, the locator actuator may be configured for automatically collapsing the positioning elements to the collapsed configuration upon advancement of the housing to prevent engagement between the closure element and the positioning elements. The housing may be substantially permanently but slidably disposed on the sheath. Alternatively, the housing may be provided separate from the sheath, e.g., with the closure element pre-loaded therein. The housing may be directed over the sheath, e.g., over the proximal end of the sheath, at any time before delivery of the closure element.

In accordance with another aspect of the present invention, a method is provided for delivering a closure element into a passage communicating with an opening in a wall of a body lumen. An introducer sheath is positioned through a patient's skin towards the body lumen via the passage, the sheath including a lumen extending between its proximal and distal ends. One or instruments may be introduced through the lumen of the sheath into the body lumen. A diagnostic or therapeutic procedure may be performed using the one or more instruments at a location accessed via the body lumen.

In a preferred embodiment, the body lumen is a blood vessel, such as a peripheral vessel, e.g., the femoral or carotid artery. The procedure may be any of a variety of endovascular procedures, such as angioplasty, atherectomy, stent delivery, delivery of a therapeutic agent, and tissue ablation.

Upon completion of the procedure, the devices may be removed from the sheath. A locator may be inserted along or through the sheath until a distal portion of the locator extends beyond the distal end of the sheath and into the body lumen. One or more positioning elements on the distal portion of the locator may be expanded from a collapsed configuration to an expanded configuration.

The sheath and locator may then be manipulated with respect to the body lumen until the positioning elements in their expanded configuration contact the wall of the body lumen, thereby providing a tactile indication of a location of the distal end of the sheath. A closure element may then be delivered via the sheath into the passage. The sheath and locator may be withdrawn from the body lumen and opening, leaving the closure element to substantially close the opening.

In a preferred embodiment, the closure device is delivered via a housing slidably attached to the sheath. The housing may be advanced distally, e.g., along an exterior of the sheath, the housing having the closure device detachably held thereto. In a preferred method, the positioning elements may automatically return to the collapsed configuration when the housing is advanced to its distal position, thereby avoiding engagement between the closure element and the positioning elements. Alternatively, the positioning elements may automatically collapse when an ejector is activated to deploy the closure element from the housing, e.g., after the housing has been advanced to its distal position.

Other objects and features of the present invention will become apparent from consideration of the following description taken in conjunction with the accompanying drawings.

BRIEF DESCRIPTION OF THE DRAWINGS

FIG. 1 is a side view of an apparatus for delivering a closure element, including an introducer sheath, a locator, and an actuator assembly, in accordance with the present invention.

FIG. 2 is a side view of the apparatus of FIG. 1, with the locator disposed within the sheath, and a housing on the sheath advanced to a delivery position.

FIGS. 3A and 3B are perspective views of the distal end of the apparatus of FIGS. 1 and 2, showing positioning elements on the locator in collapsed and expanded configurations, respectively.

FIGS. 4A–4F are cross-sectional views of a blood vessel, showing a method for delivering a closure device into a passage communicating with the vessel.

FIG. 5 is a cross-sectional view of the blood vessel of FIG. 4D, showing the positioning elements engaging a wall of the vessel.

FIG. 6 is a perspective view of an alternate embodiment of a distal portion of the locator with the positioning elements disposed in their expanded configuration.

DETAILED DESCRIPTION OF THE PREFERRED EMBODIMENTS

Figure 4A:
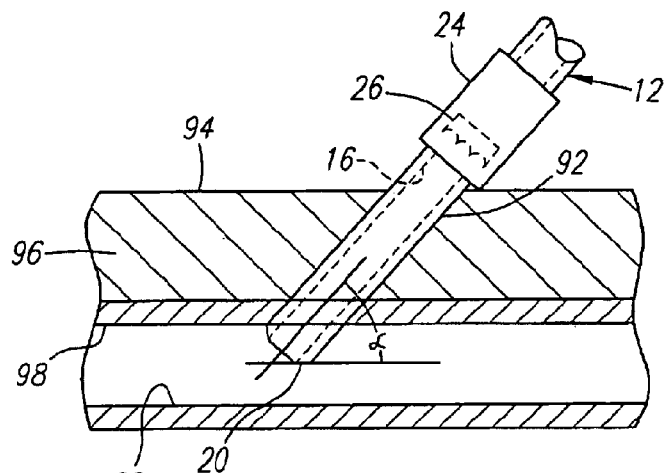

Turning now to the drawings, FIGS. 1–2 show a first preferred embodiment of an apparatus 10 for providing access into a blood vessel or other body lumen from an incision, puncture, or other passage (not shown in FIGS. 1 and 2), and/or for delivering a closure element, such as clip 26 (shown in phantom), for closing the passage. Generally, the apparatus 10 includes an introducer sheath 12, a housing 24 slidably disposed on the sheath 12, a locator member 14 insertable into the sheath 12, and an housing actuator assembly 30.

The sheath 12 includes a substantially flexible or semi-rigid tubular body 15 including a lumen 16 extending between its proximal and distal ends 18, 20. The distal end 20 has a size and shape to facilitate insertion into a blood vessel, e.g., having a tapered tip 22 for facilitating substantially atraumatic introduction through the passage and at least partially into the vessel. The lumen 16 has a size for accommodating insertion of one or more devices therethrough, such as a catheter, guidewire, and the like (not shown). The sheath 12 also preferably includes a seal (not shown), such as a hemostatic valve, within the lumen 16 at or near the proximal end 18 that provides a fluid-tight seal, yet accommodates insertion of one or more devices, such as the locator 14, into the lumen 16 without fluid passing proximally from the sheath 12.

Optionally, the sheath 12 may include a side port 19 that communicates with the lumen 16, for example, to allow the infusion of fluids into the lumen 16, through the sheath 12. Alternatively, or in addition, the side port 19 may be used to provide a "bleed back" indicator, such as that disclosed in U.S. Pat. No. 6,626,918, entitled "Apparatus and Methods for Positioning a Vascular Sheath," which is assigned to the assignee of the present invention. The disclosure of this patent and any references cited therein are expressly incorporated herein.

A housing 24 is slidably disposed on an exterior of the sheath 12, the housing 24 configured for releasably holding the closure element 26. The housing 24 may include an ejector or other mechanism (not shown) for deploying the closure element 26 from the housing 24. In a preferred embodiment, the closure element 26 is an annular-shaped clip, including one or more barbs 28 for engaging the tissue around the puncture adjacent to the wall of the vessel. Preferably, the clip 26 is configured for drawing the tissue around the puncture at the wall of the vessel substantially closed and/or for enhancing hemostasis within the puncture. Exemplary embodiments of a housing and closure element for use with an apparatus in accordance with the present invention are disclosed in co-pending application Ser. Nos. 09/478,179, 09/546,998, and 09/610,238, the disclosures of which are expressly incorporated herein by reference.

The housing 24 is actuable from the proximal end 18 of the sheath 12 (FIG. 1), for example, by housing actuator assembly 30, for advancing the closure element 26 distally during deployment. The housing 24 may be substantially permanently but slidably disposed on the sheath 12. In this embodiment, the housing actuator assembly 30 may be substantially permanently attached to the proximal end 18 of the sheath 12. The housing 24 may be coupled to the housing actuator assembly 30 such that the housing 24 may be directed axially along the exterior of the sheath.

Alternatively, the housing 24 may be provided separate from the sheath 12 (not shown), e.g., with the closure element 26 preloaded therein. In this embodiment, the housing actuator assembly 30 may also be provided separate from the sheath 12, as shown, either coupled to or separate from the housing 24. Any time before delivering the closure element 26, the housing 24 may be directed over the sheath 12, e.g., by inserting the proximal end 18 of the sheath 12. The housing actuator assembly 30 may be attached to the proximal end 18 of the sheath 12, e.g., by cooperating connectors (not shown). The housing 24 may be coupled to the housing actuator assembly 30, if not already attached, thereby preparing the housing 24 for use.

In a preferred embodiment shown in FIGS. 1 and 2, the housing actuator assembly 30 includes first and second actuator members 46, 48 that are generally movable with respect to one another. The first actuator member 46 may be connected to the proximal end 18 of the sheath 12, for example, by rods (not shown) such that the first member 46 is substantially fixed with respect to the sheath 12. A rod, cable, or other control wire 44 is coupled to and extends generally proximally from the housing 24. The control wire 44 may extend along an outer surface of the sheath 12, as shown, or alternatively may extend through a lumen (not shown) in the sheath 12 beyond the proximal end 18.

A loose end 50 of the control wire 46 may be coupled to the second actuator member 48. For example, the housing actuator assembly 30 may be advanced over the control wire 46 such that the loose end 50 passes through aperture 52 in the first member 46 and is received in a mating pocket 54 in the second member 48, as best seen in FIG. 2. The loose end 50 may be frictionally engaged within the pocket 54 or, alternatively, the loose end 50 and pocket 54 may include cooperating detents (not shown) for securing the control wire 44 to the second actuator member 48.

The second actuator member 48 may be movable with respect to the first actuator member 46 by one or more rods or rails (not shown) extending therebetween. Thus, the second actuator member 48 may be movable from a first or proximal position (not shown), located a first distance from the first actuator member 46, distally to a second or distal position (shown in FIG. 2), located a second closer distance from the first actuator member 46. When the housing actuator assembly 30 is attached to the sheath 12 with the control wire 44 coupled to the second actuator member 48, the housing 24 may be directed from a proximal position (e.g., shown in FIG. 1) to a distal or delivery position (e.g., shown in FIG. 2) when the second actuator member 48 is moved from its proximal position to its distal position.

In a preferred embodiment, the second actuator member 48 is biased to its distal position, for example, by spring 56 or other biasing element. The second actuator member 48 may be locked in its proximal position, for example, by a locking mechanism (not shown), thereby retaining the housing 24 in its proximal position. When it is desired to advance the housing 24, a button, switch, or other activation member (not shown) may be deployed to release the locking mechanism, thereby automatically directing the second actuator member 48 towards the first actuator member 46, and thereby advancing the housing 24 to its distal position, as described further below. The closure element 26 may be automatically ejected from the housing 24 once it reaches the distal position or the closure element 26 may be subsequently ejected by a separate action. It will be appreciated by those skilled in the art that other housing actuator configurations may be provided for advancing the housing 24 with respect to the sheath 12, e.g., to deliver the closure element 26.

The housing actuator assembly 30 may also include an adjustment mechanism, such as threaded bolt or knob 58. For example, the knob 58 may be provided on the first actuator member 46 such that, as the knob 58 is rotated, the first actuator member 46 may be moved axially with respect to the sheath 12. Because the first actuator member 46 may be adjusted distally or proximally with respect to the sheath 12, the distal position of the second actuator member 48 consequently may be adjusted. This, in turn, may facilitate adjusting the distal position of the housing 24, e.g., to compensate for the thickness of a particular wall of a blood vessel when a closure element 26 is delivered to close a puncture in the wall.

Turning to FIGS. 1, 2, 3A, and 3B, the locator member 14 includes a flexible or semi-rigid tubular body or other elongate rail 32 having a proximal end 34 and a distal end 36. An actuator rod or other elongate member 38 is slidably disposed with respect to the rail 32, e.g., within a lumen 33 of tubular body 32. Preferably, the locator member 14 includes an annular ridge 40 or other detent on or near its proximal end 40 that may engage a complementary-shaped pocket 42 or other cooperating detent on the sheath 12. Thus, the locator member 14 may be substantially secured axially with respect to the sheath 12.

As best seen in FIGS. 3A and 3B, a distal portion 60 of the locator member 14 includes a substantially rounded, soft, and/or flexible distal tip 62, possibly including a pigtail (not shown) that may facilitate atraumatic advancement of the distal portion 60 into a blood vessel or other body lumen. The locator member 14 preferably has a length relative to the sheath 12 such that the distal portion 60 extends beyond the distal end 20 of the sheath 12 when the locator member 14 is fully received therein, as shown in FIG. 2.

One or more, and preferably a plurality of, positioning elements 64 are provided on the distal portion 60 that may be selectively expandable between a substantially axial collapsed configuration (shown in FIG. 3A) and a substantially transverse expanded configuration (shown in FIG. 3B). Preferably, the positioning elements 64 are substantially flexible splines configured for expanding substantially transversely with respect to a longitudinal axis 13 of the apparatus 10. In one embodiment, shown in FIGS. 1 and 2, the locator member 14 includes a pair of splines 64 disposed generally opposite one another about the distal portion 60. Alternatively, as shown in FIG. 6, the locator member 14 may include four splines 64' that are substantially equally spaced about the distal portion 60. The locator member 14 may include more or fewer splines without deviating from the scope of the present invention.

Optionally, the splines 64 may include radiopaque markers (not shown) or may be at least partially formed from radiopaque material to facilitate observation of the splines 64 using fluoroscopy or other imaging systems. In addition, the housing 24 may include a radiopaque marker, e.g., at its distal end (not shown) and/or the closure element 26 may include a radiopaque marker or may be made from radiopaque material. This may facilitate monitoring the relative location of the closure element 26 to the splines 64, as described further below.

Returning to FIGS. 3A and 3B, each spline 64 preferably has a first fixed (e.g., proximal) end 64a and a second movable (e.g., distal) end 64b. The second end 64b may be axially movable towards the first end 64a to cause an intermediate region 64c of the spline 64 to expand transversely outward, thereby defining the substantially transverse expanded configuration. In a preferred embodiment, actuator rod 38 extends through the distal portion 60 and is coupled to the second end 64b of the splines 64 and/or to distal tip 62 of the locator member 14. The rod 38 may be moved axially, e.g., proximally, with respect to the rail 32 to selectively expand the splines 64 between their collapsed configuration and their expanded configuration.

A locator actuator 70 may be coupled to the locator member 14, the locator actuator 70 configured for selectively expanding the splines 64 from their collapsed configuration to their expanded configuration. For example, the locator actuator 70 may include a switch 72 that may be depressed or rotated to retract or move the rod 38 proximally, thereby expanding or deploying the splines 64. The locator actuator 70 preferably includes a lock (not shown) for securing the rod 38 in a proximal position and thereby locking the splines 64 in their expanded configuration. The lock may be released, for example, by depressing the switch 72. The locator actuator 70 may include a spring 74 or other biasing mechanism for biasing the rod 38 distally, e.g., to return the splines 64 to their collapsed configuration when the lock is released. For example, as described further below, the lock may be released upon activation of the housing actuator assembly 30, e.g., when the second actuator member 48 moves towards its distal position.

Turning to FIGS. 4A–4F, the apparatus 10 may be used to provide access into a blood vessel or other body lumen 90. Preferably, the apparatus 10 may be used to deliver a closure device, such as clip 26, to close and/or seal an incision, puncture, or other passage 92 that extends from a patient's skin 94 through intervening tissue 96, and a wall 98 of the vessel 90.

As shown in FIG. 4A, the sheath 12, without the locator member 14 therein, may be inserted or otherwise positioned within the blood vessel 90, i.e., through the passage 92. The sheath 12 is preferably provided with the housing 24 in its proximal position, without the housing actuator assembly (not shown) attached. Alternatively, the housing actuator assembly may be provided attached to the sheath 12 as long as the lumen 16 may be accessed. In a further alternative, the sheath 12 may be provided without the housing 24 thereon. The sheath 12 may be advanced over a guide wire or other rail (not shown) previously positioned through the passage 92 into the blood vessel 90 using a conventional procedure. Preferably, the blood vessel 90 is a peripheral vessel, such as a femoral or carotid artery, although other body lumens may be accessed using the sheath 12, as will be appreciated by those skilled in the art.

The passage 92, and consequently the sheath 12, may be oriented at a substantially acute angle "alpha" with respect to the vessel 90, thereby facilitating introduction of devices through the lumen 16 of the sheath 12 into the vessel 90 with minimal risk of damage to the vessel 90. One or more devices, such as a guide wire, a catheter, and the like (not shown), may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature.

After the procedure is complete, the device(s) may be removed from the sheath 12, and the locator member 14 may be inserted through the hemostatic valve (not shown) into the lumen 16. If the housing 24 is not already provided on the sheath 12, the housing 24 and/or the housing actuator assembly (not shown) may be advanced over or otherwise attached to the proximal end of the sheath 12, preferably before the locator member 14 is inserted into the sheath 12.

Figure 4B:
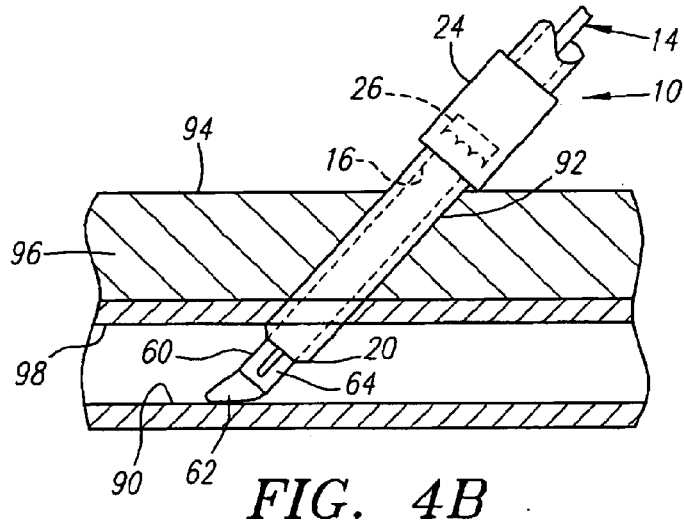

As shown in FIG. 4B, when the locator member 14 is fully inserted within the sheath 12, the distal portion 60 extends beyond the distal end 20 of the sheath 12. In an alternative embodiment, the locator member 14 may be attached to an exterior surface (not shown) of the sheath 12, for example, along a track, e.g., cooperating slots, grooves, and the like (not shown) in the sheath 12 and locator member 14. The distal tip 62 preferably is substantially soft and/or flexible such that the distal portion 60 substantially atraumatically enters the vessel 90. In this fully inserted position, cooperating detents (not shown) may be engaged to substantially secure the locator member 14 axially with respect to the sheath 12. The housing actuator assembly (not shown) may be attached to the sheath 12, e.g., by attaching a control wire (not shown) from the housing 24 to the actuator assembly, as described above.

Alternatively, the sheath 12 may include a side port (not shown) at or near its distal end 20 and a bleed back lumen (also not shown) that extends from the side port to the proximal end of the sheath 12. Before or after insertion of the locator member 14, the sheath 12 may be manipulated until "bleed back" (i.e., blood entering the side port and passing proximally through the lumen due to exposure of the side port to blood pressure within the vessel) indicates a desired position for the distal end 20 of the sheath 12. For example, the sheath 12 may be partially withdrawn from the vessel 90 before the locator member 14 is inserted into the sheath 12 to minimize contact between the vessel wall 98 and the distal portion 60 of the locator member 14 during insertion of the locator member 14 into the sheath 12.

Figure 4C:
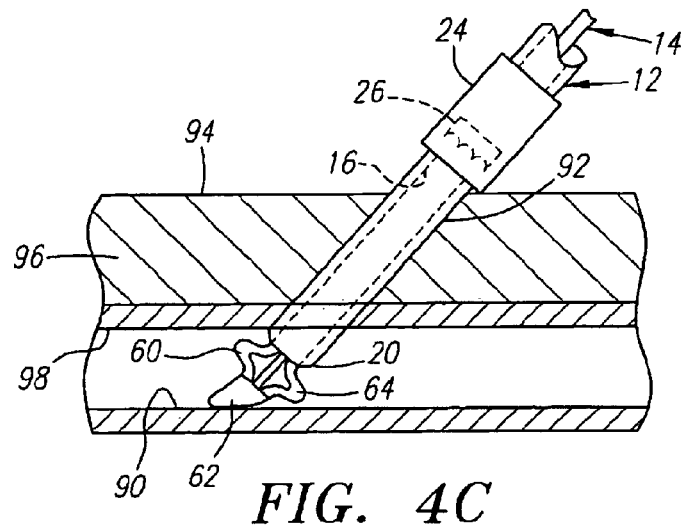
Figure 4D:
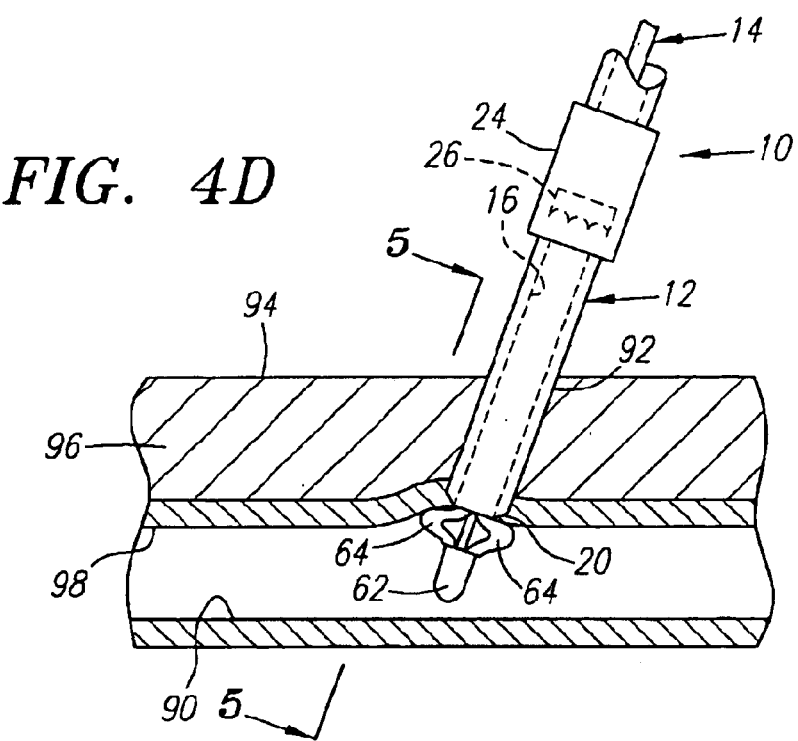

As shown in FIG. 4C, the splines 64 may then be directed to their expanded configuration, for example, by activating a switch on the proximal end (not shown) of the locator member 14. The sheath 12 and locator member 14 may then be moved in conjunction with one another, and preferably are together partially withdrawn from the vessel 90, until the splines 64 contact the wall 98 of the vessel 90, as shown in FIG. 4D. Thus, the splines 64 may provide a tactile indication of the position of the sheath 12 with respect to the wall 98 of the vessel 90. In addition, the splines 64 may assist in "presenting" the wall 98 of the vessel 90, e.g., for receiving a closure element, such as clip 26.

Figure 4E:
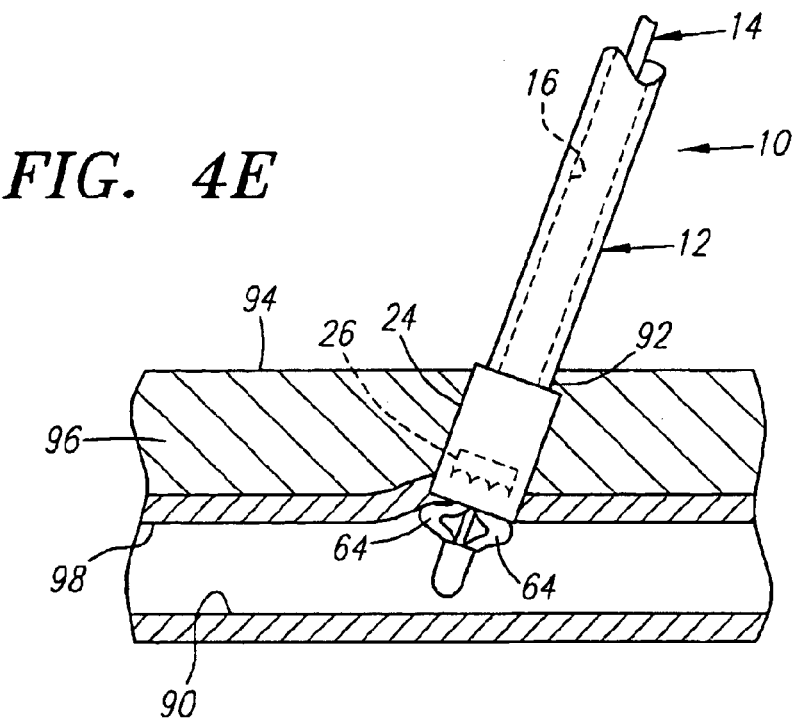

Turning to FIG. 4E, with the sheath 12 properly positioned, the housing 24 may then be actuated, for example, to advance the housing 24 distally into the passage 92 to deliver the clip 26. Preferably, movement of the housing 24 with respect to the distal end 20 of the sheath 12 is limited, e.g., by the housing actuator assembly (not shown), as described above. Preferably, the housing 24 may only be advanced a fixed distance such that the clip 26 substantially engages the wall 98 of the blood vessel, e.g., until the barbs 28 penetrate but do not pass completely through the wall 98. Thus, with the splines 64 fixed with respect to the distal end 20 of the sheath 12 and the distal position of the housing 24 fixed, the clip 26 may be advanced a predetermined distance into the passage 92 that is ascertainable and predictable. This predetermined distance may facilitate proper deployment of the clip 26 with respect to the wall 98 of the vessel 90, e.g., to prevent advancement of the clip 26 too far, i.e., into the vessel 90.

Alternatively, or in addition, the splines 64 include radiopaque markers, such that fluoroscopy and the like may be used to monitor and position the distal portion 60 of the locator member 14. The housing 24 and/or closure element 26 may also include radiopaque markers such that a relative position of the closure element 26 with respect to the splines 64, and consequently to the wall 98 of the vessel 90, may be ascertained before the closure element 26 is deployed from the housing 24.

In a preferred method, the splines 64 automatically return to their collapsed configuration when the closure element 26 is deployed from the housing 24 or when the housing 24 reaches its distal position, as shown in FIG. 4F. For example, the housing actuator assembly (not shown) may contact the locator actuator (also not shown) when the housing actuator assembly is used to advance the housing 24 to its distal position, thereby releasing the locator actuator. This enhancement may avoid any risk of contact between the clip 26 and the splines 64, e.g., which otherwise may risk driving the barbs 28 of the clip 26 through the wall 98 of the vessel 90 and into the splines 64. Alternatively, or in addition, the distal portion 60 of the locator member 14 may be automatically retracted, e.g., into the sheath 12, when the closure element 26 is deployed or the housing 24 is advanced.

Once the clip 26 is successfully deployed within the passage 92, i.e., into the wall 98 of the vessel 90, the apparatus 10 may be withdrawn from the passage 92. If the splines 64 of the locator member 14 are not automatically collapsed during advancement of the housing 24, the splines 64 may first be affirmatively collapsed, e.g., by depressing the locator actuator (not shown). The entire apparatus 10 may then be removed in one step, or alternatively, the locator member 14 may first be withdrawn from the sheath 12 before withdrawing the sheath 12, thereby leaving the clip 26 in place to close and/or seal the passage 92.

Figures 7A, 7B:
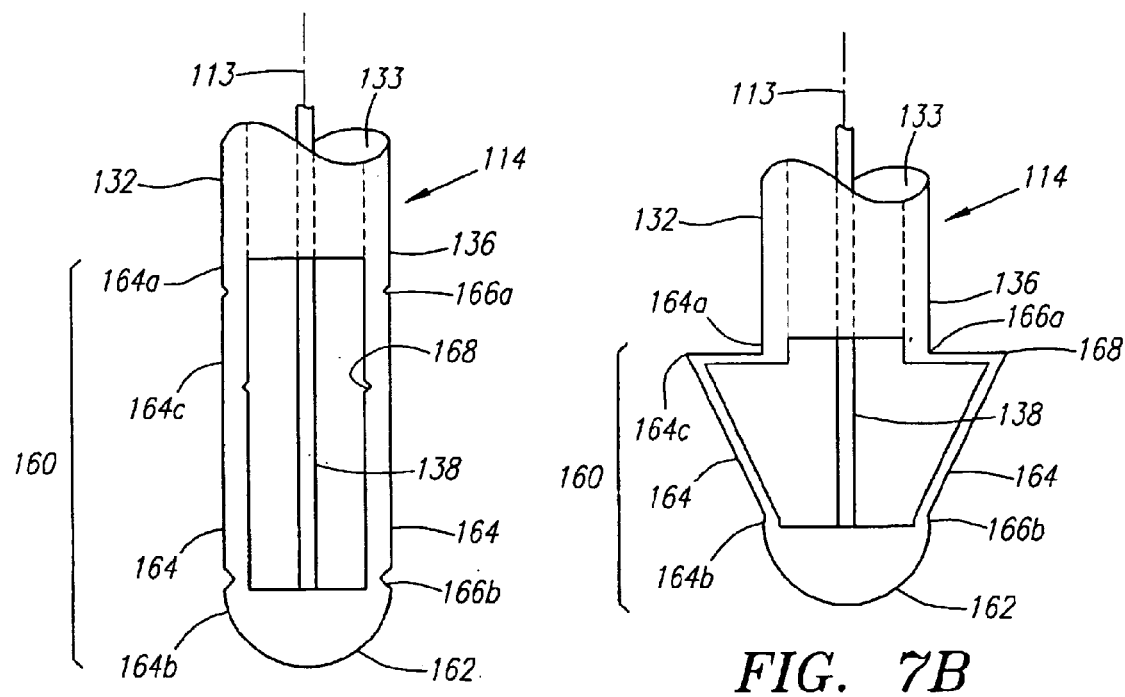
FIGS. 7A and 7B are side views of another embodiment of a distal portion of a locator with positioning elements disposed in collapsed and expanded configurations, respectively.

Turning to FIGS. 7A and 7B, another embodiment of a distal portion 160 of a locator member 114 is shown that may be used to position a sheath (not shown) before delivering a closure element (also not shown), similar to the embodiment described above. The locator member 114 includes a flexible or semi-rigid tubular body 132 having a proximal end (not shown) and a distal end 136. An actuator wire or rod 138 is slidably disposed with respect to the body 132, e.g., within a lumen 133 of body 132. The locator member 114 may include a detent (not shown) on or near its proximal end for securing the locator member 114 to a sheath (not shown).

The locator member 114 includes a distal portion 160 that terminates in a substantially rounded, soft, and/or flexible distal tip 162, possibly including a pigtail (not shown) that may facilitate atraumatic advancement of the distal portion 160 into a blood vessel or other body lumen. The locator member 114 preferably has a length relative to the sheath such that the distal portion 160 extends beyond a distal end of the sheath when the locator member 114 is fully received in the sheath, similar to the embodiment described above.

A plurality of splines 164 are provided on the distal portion 160 that may be selectively expandable between a substantially collapsed configuration (shown in FIG. 7A) and a substantially transverse expanded configuration (shown in FIG. 7B). Preferably, the splines 164 are substantially rigid or semi-rigid elements that include hinged regions 166a, 166b and 168 that facilitate expansion substantially transversely with respect to a longitudinal axis 113 of the locator member 114. In one embodiment, each spline 164 is a single piece that includes a plurality of living hinges 166a, 166b and 168. Alternatively, each spline 164 may include multiple segments that are connected by pins or other hinges (not shown). In a preferred embodiment, the distal portion 160 includes four equally spaced splines 164, although the locator member 14 may include more or fewer spines without deviating from the scope of the present invention. Optionally, the splines 164 may include radiopaque markers (not shown), similar to the embodiment described above.

Each spline 164 preferably has a first fixed end 164a and a second movable end 164b. The second end 164b may be axially movable towards the first end 164a to cause an intermediate region 164c of the spline 64 to expand transversely outward, thereby defining the substantially transverse expanded configuration. In a preferred embodiment, the actuator rod 138 extends through the distal portion 160 and is coupled to the second end 164b of the splines 164 and/or to distal tip 162 of the locator member 114. The rod 138 may be moved axially with respect to the body 132 to selectively expand the splines 164 between the collapsed and expanded configurations.

Figures 8A, 8B:
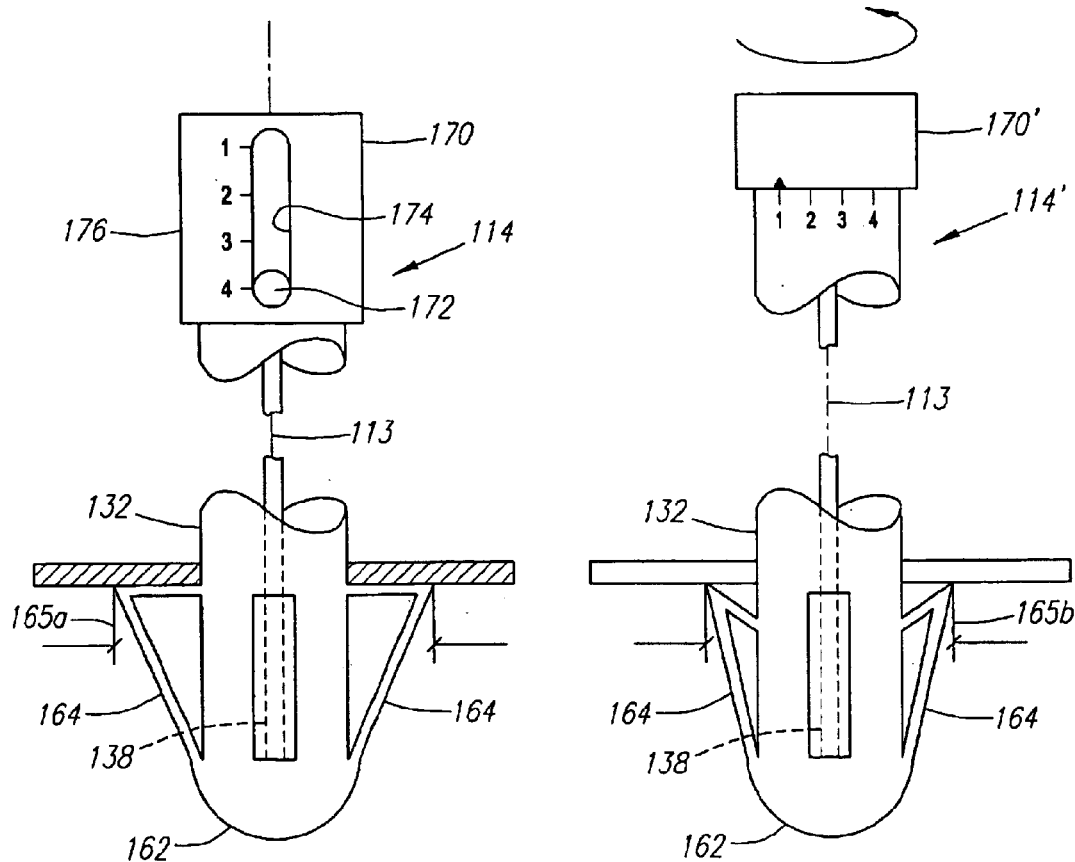
FIGS. 8A and 8B are side views of the locator of FIGS. 7A and 7B, including a control on the locator for adjusting the expansion of the positioning elements.

Turning to FIG. 8A, a locator actuator 170 may be coupled to the control rod 138 and a proximal end 134 of the locator member 114. The locator actuator 170 is configured for directing the control rod 138 axially to selectively expand the splines 164, similar to the embodiment described above.

In addition, the locator actuator 170 may allow the splines 164 to be expanded to one of a plurality of expanded configurations. For example, the locator actuator 170 may include an internal member (not shown), coupled to the control rod 138, that is slidable within an actuator body 176. A button 172 extending from the internal member is slidable in an axial slot 174 in the actuator body 176 for controlling movement of the control rod 138. The button 172 may be moved, thereby moving the control rod 138 and consequently moving the splines 164. For example, as shown in FIG. 8A, the button 172 may be moved to a position (for example, indicated as "4") thereby expanding the splines 164 to an expanded diameter 165a. If desired, the button 172 may be moved to other available positions to reduce the expanded diameter, for example to the diameter 165b shown in FIG. 8B. This control of the expanded diameter of the splines 164 may be useful to allow the splines 164 to be deployed within body lumens of different sizes. Thus, the splines 164 may be expanded to a desired size corresponding to the size of the vessel into which the locator 114 is introduced, thereby minimizing the risk of damage to the vessel due to over expansion of the splines 164.

In an alternative embodiment, shown in FIG. 8B, the locator actuator 170' may include a rotatable dial that controls expansion of the splines 164, similar to the linear actuator 170 shown in FIG. 8A. In addition, the locator actuator 170, 170' may include demarcations indicating a size (not shown), e.g., a diameter of the expanded splines and/or the size of the body lumen corresponding to the size of the lumen into which the locator 114 is to be introduced.

Figure 9:
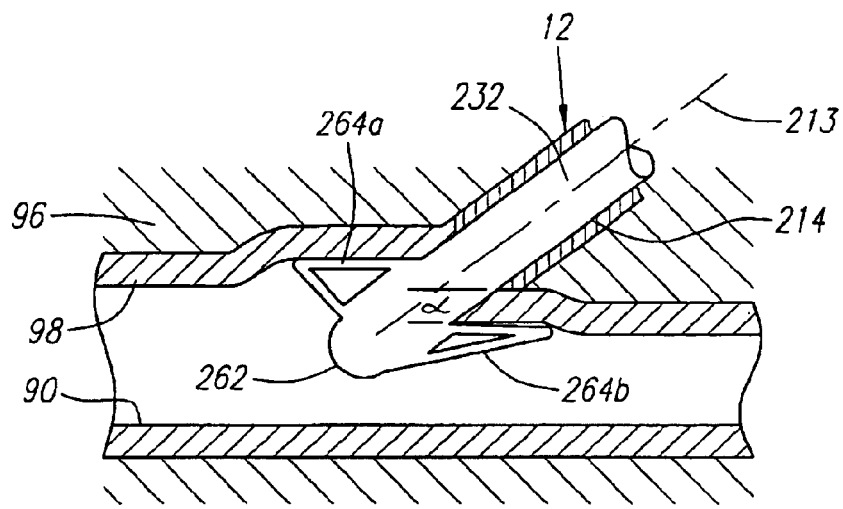
FIG. 9 is a cross-section view of a distal portion of an alternative embodiment of an apparatus for delivering a closure element, in accordance with the present invention.

In a further alternative, shown in FIG. 9, a locator member 214 may be provided that includes splines 264a, 264b that may be selectively expanded to different angles. A locator actuator (not shown) may allow controlled expansion of the splines 264a, 264b to desired angles with respect to the longitudinal axis 213 of the locator member. For example, a cable or other control wire (not shown) may be extend from the locator actuator to each of the splines 264a, 264b, e.g., through a lumen (not shown) in the locator body 232. Each cable may be directed axially to selectively expand or collapse the spline 264a, 264b connected to the respective cable.

For example, a spline 264b on the posterior side of the locator member 214 (away from the surface of the patient's skin) may be expanded towards the proximal end of the locator member 214 at an acute angle "alpha," i.e., corresponding substantially to the angle of the passage through the patient's skin to the vessel 90, e.g., about thirty or forty five degrees. In contrast, the spline 264a on the anterior side of the locator member 214 (i.e. towards the surface of the patient's skin) may be expanded away from the proximal end of the locator member 214 at an oblique angle of one hundred eighty degrees less "alpha." Thus, the splines 264a, 264b may be expanded to predetermined angles that facilitate better contact with the wall of the vessel, e.g., to better "present" the vessel wall during deployment of a closure element.

Figure 10:
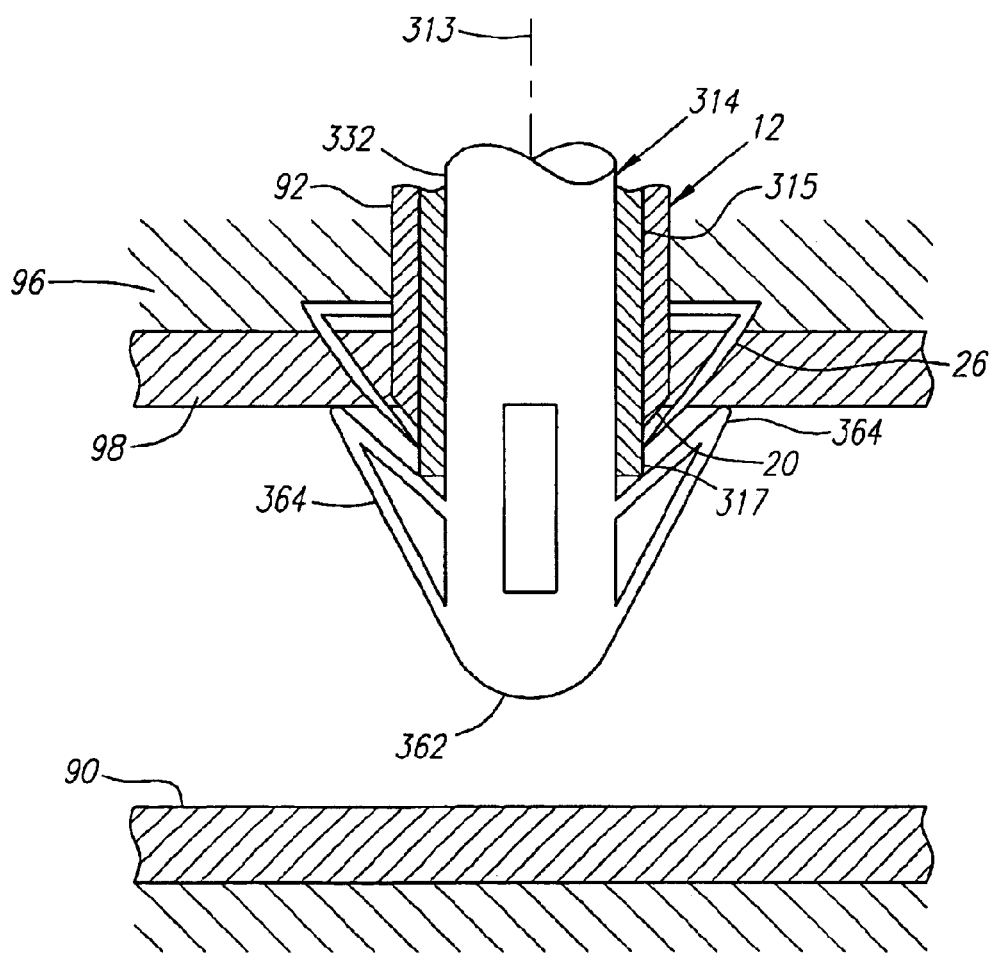
FIG. 10 is a cross-sectional view of a distal portion of yet another alternative embodiment of an apparatus for delivering a closure element, in accordance with the present invention.

In yet another alternative embodiment, shown in FIG. 10, a locator member 314, such as those described above, may include a tubular sleeve 315 within which a body 332, including splines 364, may be axially directed. For example, a proximal end (not shown) of the sleeve 315 may be fixed to a proximal end (also not shown) of the body 332, e.g., to a locator actuator (not shown), such as those described above. At least a distal portion 317 of the sleeve 315 is formed from a substantially rigid, smooth walled tube, such as a hypotube, while the remainder of the sleeve 315 may be a portion of the same tube or may be formed from a substantially flexible or semi-rigid tubular member (not shown).

When the locator member 314 is fully inserted into an introducer sheath 12, such as those described above, the distal portion 317 of the sleeve 315 extends beyond a distal end 20 of the sheath 12. The splines 364 may then be selectively deployed from within the sleeve 315, expanded to a substantially transverse expanded configuration, collapsed, and retracted back into the sleeve 315.

For example, the sheath 12 maybe positioned through a puncture 92 into a vessel 90, e.g., to perform a procedure within a patient's vasculature, as described above. The locator member 314 may then be inserted into the sheath 12 until the distal portion 317 extends beyond the distal end 20 of the sheath 12. The splines 364 may then be expanded, and the sheath 12 and locator member 314 manipulated to a desired position, e.g., such that the splines 364 contact the wall 98 of the vessel 90, thereby providing a tactile indication of the position of the sheath 12.

A closure element, such as clip 26 may then be deployed, e.g., from a housing (not shown) slidably mounted on the sheath 12. Barbs or tines 28 on the clip 26 penetrate into the wall 98 of the vessel 90, e.g., to close the opening in the wall 98 of the vessel 90, as described above. If the barbs 28 penetrate completely through the wall 98 of the vessel 90, the sleeve 315 protects the splines 364 and/or the body 33 of the locator member 314. The barbs 28 may engage but not penetrate or otherwise catch on the distal portion 317 of the sleeve 315, because of its substantially rigid and/or smooth construction. Thus, the barbs 28 may not penetrate or otherwise catch on the splines 364 when the clip 26 is deployed. The splines 364 may be collapsed and retracted into the sleeve 315, either manually or automatically, similar to the embodiments described above. When the sheath 12 is withdrawn from the puncture 92, the barbs 28 may slide along the distal portion 317 of the sleeve 315 until the distal portion 317 is withdrawn from within the clip 26, whereupon the barbs 28 may move inwards to close and/or seal the opening in the wall 98 of the vessel 90.

In alternative embodiments, the apparatus and methods of the present invention may be used to locate an introducer sheath within a blood vessel and/or to deliver closure elements other than a clip. For example, the apparatus may be used to deliver a collagen plug and the like into the passage, or a sealing material (either alone, or in conjunction with a clip).

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering a closure element into a passage communicating with an opening into a body lumen, comprising:

an elongate member comprising proximal and distal ends;

an annular clip carried by the elongate member for closing the opening;

a locator member coupled to the elongate member, the locator member having a distal portion extending distally beyond the distal end of the elongate member;

one or more positioning elements on the distal portion of the locator member, the positioning elements being selectively expandable between a substantially axial collapsed configuration and a substantially transverse expanded configuration; and a housing slidably disposed on the exterior of the elongate member, the housing configured for housing the clip and releasably holding the clip therein, the housing being actuable for advancing the clip distally towards the distal end of the elongate member.

2. The apparatus of claim 1, wherein the positioning elements comprise splines configured for expanding substantially transversely with respect to a longitudinal axis of the elongate member.

3. The apparatus of claim 2, wherein the one or more positioning elements comprise a plurality of substantially flexible splines.

4. The apparatus of claim 2, wherein the one or more positioning elements comprise a pair of splines disposed opposite one another about the distal portion.

5. The apparatus of claim 2, wherein each spline has a first fixed end and a second movable end, the second end being axially movable towards the first end to cause an intermediate region of the spline to expand transversely outward, thereby defining the substantially transverse expanded configuration.

6. The apparatus of claim 5, wherein the locator member comprises a control member having a distal end coupled to the second end of each spline, the control member being movable axially with respect to the elongate member to selectively expand the splines between the collapsed configuration and the expanded configuration.

7. The apparatus of claim 1, further comprising an actuator coupled to the locator member, the actuator configured for selectively expanding the positioning elements from the collapsed configuration to the expanded configuration.

8. The apparatus of claim 7, wherein the actuator is configured for selectively expanding the positioning elements to one of a plurality of expanded diameters.

9. The apparatus of claim 7, wherein the actuator is configured for selectively expanding the positioning elements to a desired angle with respect to a longitudinal axis of the locator member.

10. The apparatus of claim 9, wherein opposing positioning elements may be expanded to complementary angles with respect to the longitudinal axis.

11. The apparatus of claim 1, further comprising an actuator coupled to the housing, the actuator configured for advancing the housing distally to deploy the clip therefrom.

12. The apparatus of claim 11, wherein the actuator is further configured for automatically collapsing the positioning elements to the collapsed configuration upon advancement of the housing.

13. The apparatus of claim 11, further comprising a spring mechanism for biasing the housing distally upon activation of the actuator.

14. The apparatus of claim 1, wherein the elongate member comprises an introducer sheath including a lumen therethrough, and wherein the locator member is removably insertable into the lumen, the distal portion of the locator member having a size for insertion through the lumen when the positioning members are in the collapsed configuration.

15. The apparatus of claim 14, wherein the sheath and the locator member include cooperating detents for substantially securing the locator member axially with respect to the sheath when the locator member is fully inserted into the sheath.

16. The apparatus of claim 14, wherein the locator member comprises a substantially rigid sleeve extending beyond the distal end of the sheath, the positioning elements being deployable axially from within the sleeve.

17. An apparatus for delivering an annular clip into a passage communicating with an opening into a body lumen, comprising:
an elongate member comprising proximal and distal ends;
a housing slidable along an exterior of the elongate member, the housing configured for releasably holding annular clip therein;
a locator member comprising a distal portion extending distally beyond the distal end of the elongate member; and
one or more positioning elements on the distal portion of the locator member, the positioning elements being selectively expandable between a substantially axial collapsed configuration and a substantially transverse expanded configuration.

18. The apparatus of claim 17, wherein the elongate member and the locator member include cooperating detents for substantially securing the locator member axially with respect to the elongate member.

19. The apparatus of claim 17, further comprising an actuator coupled to the housing, the actuator configured for advancing the housing distally to deploy an annular clip therefrom.

20. The apparatus of claim 19, wherein the actuator is further configured for automatically collapsing the positioning elements to the collapsed configuration upon advancement of the housing.

21. The apparatus of claim 19, further comprising a spring mechanism for biasing the housing distally upon activating the actuator.

22. The apparatus of claim 17, wherein each positioning element comprises a spline having a first fixed end and a second movable end, the second end being axially movable towards the first end to cause an intermediate region of the spline to expand transversely outward, thereby defining the substantially transverse expanded configuration.

23. The apparatus of claim 17, further comprising an actuator coupled to the locator member, the actuator configured for selectively expanding the positioning elements from the collapsed configuration to the expanded configuration.

24. The apparatus of claim 23, wherein the actuator is configured for selectively expanding the positioning elements to one of a plurality of expanded diameters.

25. The apparatus of claim 17, wherein the elongate member comprises an introducer sheath, and wherein the locator member is insertable into a lumen of the sheath.

26. An apparatus for delivering a closure element into a passage communicating with an opening into a body lumen, comprising:
a tubular member comprising proximal and distal ends;
an annular housing overlying the tubular member and slidable towards the distal end of the tubular member;
an annular clip releasably carried within the housing; and
a locator member within the tubular member, the locator member having a distal portion extending distally beyond the distal end of the tubular member, the distal portion comprising a plurality of positioning elements, the positioning elements being selectively expandable between a substantially axial collapsed configuration and a substantially transverse expanded configuration.

27. The apparatus of claim 26, wherein the locator member is insertable into the tubular member, the locator member and tubular member comprising cooperating detents for substantially securing the locator member with respect to the tubular member.

28. The apparatus of claim 26, further comprising an actuator coupled to the housing for advancing the housing and the closure element therein towards the distal end of the tubular member for deploying the closure element from the housing.

29. The apparatus of claim 28, wherein the actuator is configured for automatically collapsing the positioning elements when the housing reaches a distal position for deploying the closure element.

30. The apparatus of claim 29, wherein the actuator is configured for retracting the positioning elements into the tubular member when the closure element is deployed from the housing.

31. A method for delivering a closure element into a passage communicating with an opening in a wall of a body lumen, the method comprising:

positioning an elongate member through a patient's skin towards the body lumen via the passage, the elongate member including a lumen extending between its proximal and distal ends; and providing a locator comprising a distal portion extending beyond the distal end of the elongate member and into the body lumen;

expanding one or more positioning elements on the distal portion of the locator from a collapsed configuration to an expanded configuration;

withdrawing the elongate member and locator partially until the positioning elements in their expanded configuration contact the wall of the body lumen, thereby providing a tactile indication of a location of the distal end of the elongate member; and delivering a clip located in a housing slidably mounted on the elongate member via the elongate member into the passage by advancing the housing distally along the exterior of the elongate member, the housing releasably holding the clip therein.

32. The method of claim 31, further comprising withdrawing the elongate member and locator from the body lumen and opening, leaving the clip to substantially close the opening.

33. The method of claim 31, wherein the elongate member comprises an introducer sheath, and wherein the method further comprises introducing one or more instruments through the lumen of the sheath into the body lumen.

34. The method of claim 33, further comprising performing a diagnostic or therapeutic procedure using the one or more instruments at a location accessed via the body lumen.

35. The method of claim 34, wherein the body lumen comprises a blood vessel, and wherein the procedure comprises at least one of angioplasty, atherectomy, stent delivery, delivery of a therapeutic agent, and tissue ablation.

36. The method of claim 31, wherein the elongate member comprises a tubular body, wherein the locator is inserted into the tubular body and is axially fixed with respect to the tubular body when the locator is fully inserted into the tubular body.

37. The method of claim 31, wherein the housing is movable between a proximal position and a distal position, the distal position being a predetermined distance from the positioning elements in their expanded configuration.

38. The method of claim 37, wherein the positioning elements automatically return to the collapsed configuration when the housing is advanced to the distal position.

39. The method of claim 31, further comprising collapsing the one or more positioning elements to the collapsed configuration before withdrawing the elongate member and locator.

40. The method of claim 31, wherein the housing comprising a cavity carrying the clip therein, and wherein the delivering step comprises deploying the clip from the cavity.

41. The method of claim 31, wherein the one or more positioning elements comprise a pair of opposing splines on the distal portion, the splines being expandable from a substantially axial collapsed configuration to a substantially transverse expanded configuration.

* * * * *